(12) United States Patent
Kong et al.

(10) Patent No.: US 12,029,409 B2
(45) Date of Patent: Jul. 9, 2024

(54) SUTURE ANCHOR

(71) Applicant: BEIJING DELTA MEDICAL SCIENCE & TECHNOLOGY CORP., LTD., Beijing (CN)

(72) Inventors: Qingjun Kong, Beijing (CN); Jianbo Li, Beijing (CN); Juwei Wang, Beijing (CN); Teng Gao, Beijing (CN)

(73) Assignee: BEIJING DELTA MEDICAL SCIENCE & TECHNOLOGY CORP., LTD., Beijing (CN)

( * ) Notice: Subject to any disclaimer, the term of this patent is extended or adjusted under 35 U.S.C. 154(b) by 500 days.

(21) Appl. No.: 17/523,897

(22) Filed: Nov. 10, 2021

(65) Prior Publication Data
US 2022/0354481 A1 Nov. 10, 2022

Related U.S. Application Data

(63) Continuation of application No. PCT/CN2021/112401, filed on Aug. 13, 2021.

(30) Foreign Application Priority Data

May 10, 2021 (CN) .......................... 202110507883.5

(51) Int. Cl.
*A61B 17/04* (2006.01)
(52) U.S. Cl.
CPC .. *A61B 17/0401* (2013.01); *A61B 2017/0403* (2013.01); *A61B 2017/0448* (2013.01); *A61B 2017/0458* (2013.01)
(58) Field of Classification Search
CPC ........ A61B 17/0401; A61B 2017/0403; A61B 2017/0448; A61B 2017/0458; A61B 2017/0414; A61B 2017/0456; A61B 2017/0425; A61B 17/8605; A61B 2017/0412; A61B 17/701; A61B 2017/044
See application file for complete search history.

(56) References Cited

U.S. PATENT DOCUMENTS

| | | | | | |
|---|---|---|---|---|---|
| 5,464,427 | A | * | 11/1995 | Curtis | A61B 17/0401 606/313 |
| 5,707,395 | A | * | 1/1998 | Li | A61F 2/0811 606/232 |
| 7,867,264 | B2 | * | 1/2011 | McDevitt | A61F 2/0805 606/301 |
| 2005/0075668 | A1 | * | 4/2005 | Lizardi | A61B 17/0401 606/232 |
| 2013/0267998 | A1 | * | 10/2013 | Vijay | A61B 17/0401 606/232 |

FOREIGN PATENT DOCUMENTS

CN 112494089 A 3/2021

* cited by examiner

*Primary Examiner* — Mohamed G Gabr
*Assistant Examiner* — Aman Kumar Mann

(57) ABSTRACT

The present application relates to the field of medical devices, and in particular to a suture anchor. A suture anchor includes an anchor head and an anchor body, wherein a threading hole is formed on the anchor head, the anchor body includes a side pressing portion integrally formed by a plurality of layers of round tables, and at least two opposite longitudinal cuts are formed on each round table of the side pressing portion; from a direction close to the anchor head to a direction away from the anchor head, positions of the longitudinal cuts on adjacent round tables are deflected toward a same side.

7 Claims, 6 Drawing Sheets

SUTURE ANCHOR

CROSS-REFERENCE TO RELATED APPLICATION

The present application is a continuation of international application of PCT application No. PCT/CN2021/112401 filed on Aug. 13, 2021, which claims the priority benefit of China application No. 202110507883.5 filed on May 10, 2021. The entirety of the above-mentioned patent applications is incorporated herein by reference and made a part of this specification.

TECHNICAL FIELD

The present application relates to the field of medical devices, and in particular to a suture anchor.

DESCRIPTION OF RELATED ART

The suture anchor is clinically used to reconnect a soft tissue and a bone through a suture thread, the anchor is buried in the bone for fixation, and the suture thread carried on the anchor cooperates with a suture needle to fix the soft tissue. The existing suture anchor includes an anchor head and an anchor body, wherein the anchor head has a threading hole, and the suture thread passes through the threading hole. The anchor body is a multi-layer cone-tower structure, so when the anchor head is buried in a groove opened on the bone and then the anchor body is inserted into the groove, an outer ring of the anchor body will abut against the inner wall of the groove for fixation, so that the anchor head cannot escape from the groove.

For the above-mentioned related technologies, the suture thread needs to pass through the groove from the position between the anchor body and the inner wall of the groove opened on the bone for the doctor to operate. The suture thread is easily damaged and broken when it receives a squeezing between the edge position of the cone-tower structure of the anchor body and the inner wall of the groove.

SUMMARY

In order to facilitate the fixing of the suture thread without breaking the suture thread due to squeezing, the present application provides a suture anchor.

The suture anchor according to the present application adopts the following technical solutions.

A suture anchor includes an anchor head and an anchor body, wherein a threading hole is formed on the anchor head, the anchor body includes a side pressing portion integrally formed by a plurality of layers of round tables, and at least two opposite longitudinal cuts are formed on each round table of the side pressing portion; from a direction close to the anchor head to a direction away from the anchor head, positions of the longitudinal cuts on adjacent round tables are deflected toward a same side.

By adopting the above technical solution, the anchor head and the anchor body are connected to an anchor operating handle, then the suture thread is passed through the threading hole, and the anchor head and the anchor body are pushed into the groove opened on the bone through the anchor operating handle. The outer ring of the abutment portion and the inner wall of the bone groove abut and fit for fixation. The suture thread passes through the bone groove from the position where the longitudinal cuts are formed on the anchor body. Since the longitudinal cuts of each layer are not arranged in a whole row and they are arranged in a deflection manner, when the suture thread is stretched and straightened, the suture thread will pass through the center position of parts of the longitudinal cuts and also pass through the edge position of parts of the longitudinal cuts. The position of the edge parts of the longitudinal cuts will cooperate with the inner wall of the bone groove to squeeze and fix the suture thread without causing the suture thread to break.

Preferably, the positions of the longitudinal cuts on adjacent round tables are deflected by a same angle in a clockwise or counterclockwise direction from a top view, and a deflection angle of the longitudinal cuts on the adjacent round tables is from 0 to 45 degrees.

By adopting the above technical solution, the positions of the longitudinal cuts on the adjacent round tables are set at the same deflection angle, so that the staggered positions formed by the longitudinal cuts between adjacent round tables just match and fix the suture thread. The thicker the suture thread used, the larger the deflection angle.

Preferably, at least four longitudinal cuts are formed uniformly on each round table of the side pressing portion along a circumferential circle.

By adopting the above technical solution, at least four longitudinal cuts are provided in a circle around the round table so that the suture thread can pass through the bone groove at the position of the longitudinal cuts when the suture thread is stretched in each direction, without the need for deliberately adjusting the position of the suture thread during the surgery.

Preferably, the anchor body further includes an abutment portion located at an end of the side pressing portion close to the anchor head, the abutment portion has a round table shape, and a taper of the abutment portion is greater than that of the round table of the side pressing portion.

By adopting the above technical solution, the abutment portion of the anchor body is set to be a round table structure with a taper greater than that of the round table of the side pressing portion, and the anchor head is abutted and fixed by the abutment portion.

Preferably, a first arc surface that is concave from both sides to the middle is formed on bottom of the anchor head, and a second arc surface that protrudes from both sides to the middle is formed on top of the abutment portion, and the second arc surface and the first arc surface fit with each other when being abutted tightly.

By adopting the above technical solution, the first arc surface formed on the bottom of the anchor head and the second arc surface of the abutment portion cooperate, so that when the first arc surface and the second arc surface abut, the mating angle of the anchor head and the anchor body is also determined.

Preferably, the number of longitudinal cuts on each layer round table of the side pressing portion is two; when the first arc surface abuts on the second arc surface, a side edge of a longitudinal cut on the round table nearest to the anchor head directly faces the threading hole, and the other side edge of the longitudinal cut on the round table furthest from the anchor head directly faces the threading hole.

By adopting the above technical solution, when the matching angle of the anchor head and the anchor body is determined, only two longitudinal cuts are provided on each layer round table to match the suture thread for passing out. Since the complete structure of the side pressing portion is retained as much as possible, the structural strength of the side pressing portion is better and is not easily damaged.

Preferably, a plurality of oblique cuts are uniformly formed on a circumference of the abutment portion in a circumferential direction, and a cutting depth of the oblique cut at a position near a lower end of the abutment portion is greater than a cutting depth at a position near a top end of the abutment portion.

By adopting the above technical solution, oblique cuts are provided on the abutment portion to avoid the suture thread.

Preferably, the top of the anchor head is a convex arc shape.

By adopting the above technical solution, the top of the anchor head is set to be a circular arc shape, so that the anchor head will not be embedded into the bottom surface of the bone groove after being squeezed.

Preferably, a screw hole is formed on the bottom of the anchor head.

By adopting the above technical solution, the screw hole is provided on the bottom of the anchor head to cooperate with the anchor operating handle. At the same time, after the anchor operating handle pushed the anchor head and the anchor body to the position, the anchor operating handle can be rotated. After the anchor operating handle is separated from the anchor head, the anchor operating handle is pulled out.

In summary, the present application includes at least one of the following beneficial technical effects.

1. The suture thread will pass through the center position of parts of the longitudinal cuts and also pass through the edge position of parts of the longitudinal cuts. The position of the edge parts of the longitudinal cuts will cooperate with the inner wall of the bone groove to squeeze and fix the suture thread without causing the suture thread to break.

2. In a case where the matching angle of the anchor head and the anchor body is determined, only two longitudinal cuts are provided on each layer round table to match the suture thread for passing out. Since the complete structure of the side pressing portion is retained as much as possible, the structural strength of the side pressing portion is better and is not easily damaged.

3. The screw hole is provided on the bottom of the anchor head to cooperate with the anchor operating handle. At the same time, after the anchor operating handle pushed the anchor head and the anchor body to the position, the anchor operating handle can be rotated. After the anchor operating handle is separated from the anchor head, the anchor operating handle is pulled out.

DESCRIPTION OF THE EMBODIMENTS

The present application will be described in further detail below with reference to FIGS. 1-7.

The present application embodiment discloses a suture anchor.

Embodiment 1

Figure 1:
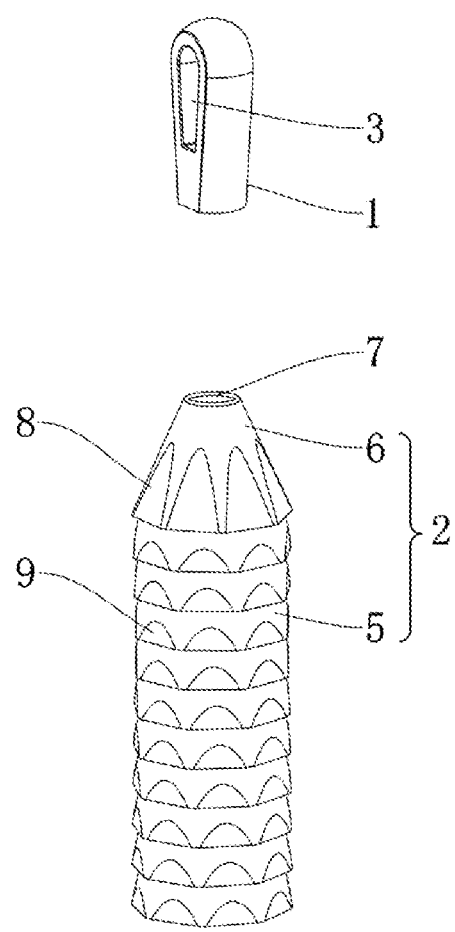
FIG. 1 is a schematic diagram of the structure according to a first embodiment.
Figure 2:
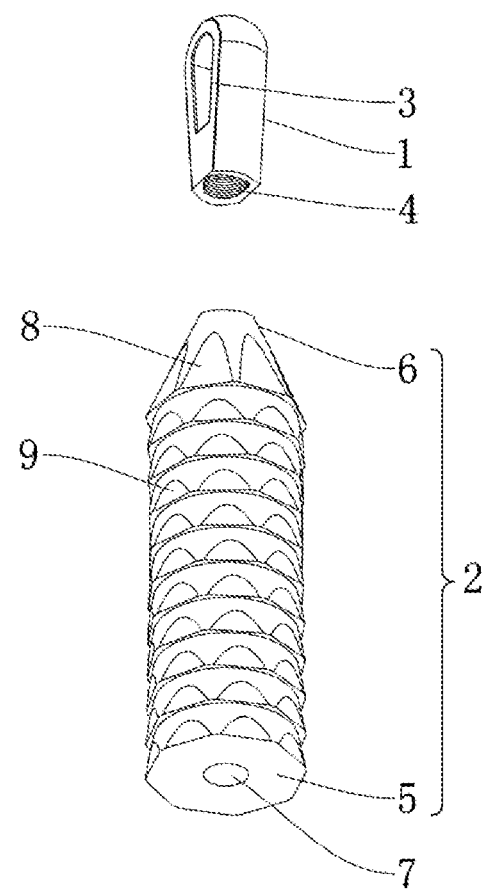
FIG. 2 is a schematic diagram of the structure according to the first embodiment from another perspective.

As shown in FIGS. 1 and 2, a suture anchor includes an anchor head 1 and an anchor body 2, the top of the anchor head 1 is a convex arc shape, a threading hole 3 is formed on the front face of the anchor head 1, and a screw hole 4 is formed on the bottom of the anchor head 1.

As shown in FIGS. 1 and 2, the anchor body 2 includes a side pressing portion 5 integrally formed by ten layers of round tables, and an abutment portion 6 integrally formed on the top of the side pressing portion 5. A through hole 7 for passing through an anchor operating handle is formed in the middle of the anchor body 2. The abutment portion 6 has a round table shape, and the taper of the abutment portion 6 is greater than that of the side pressing portion 5.

As shown in FIGS. 1 and 2, eight oblique cuts 8 are uniformly formed on a circumference of the abutment portion 6 in a circumferential direction. Each oblique cut 8 has a shallow cutting depth at a position close to the top end of the abutment portion 6, and a deep cutting depth at a position close to the lower end of the abutment portion 6. Eight longitudinal cuts 9 are uniformly formed on a circumference of each round table of the side pressing portion 5 in the circumferential direction, and each longitudinal cut 9 cuts the round table of the abutment portion 6 in the vertical direction. The positions of the longitudinal cuts 9 on the adjacent round tables from top to bottom have a small angular deflection toward the same direction.

Specific use process is as follows.

In use, the anchor head 1 and the anchor body 2 are connected to the anchor operating handle, the suture thread is passed through the threading hole 3, and the anchor head 1 and the anchor body 2 are pushed into a groove opened on the bone with the anchor operating handle.

The outer ring of the abutment portion 6 abuts on and fits to the inner wall of the bone groove for fixation. The anchor head 1 abuts on the anchor body 2. The suture thread passes through the bone groove from a position where the longitudinal cuts 9 are formed on the anchor body 2. Since the positions of the longitudinal cuts 9 on each layer are deflected relative to each other, when the suture thread is stretched and straightened outwards, the suture thread can pass through a part with a larger gap between the abutment portion 6 and the bone groove, and can also pass through a part with a smaller gap therebetween, so that the suture thread is firmly fixed and cannot be cut off by the edge of the round table.

Embodiment 2

Figure 3:
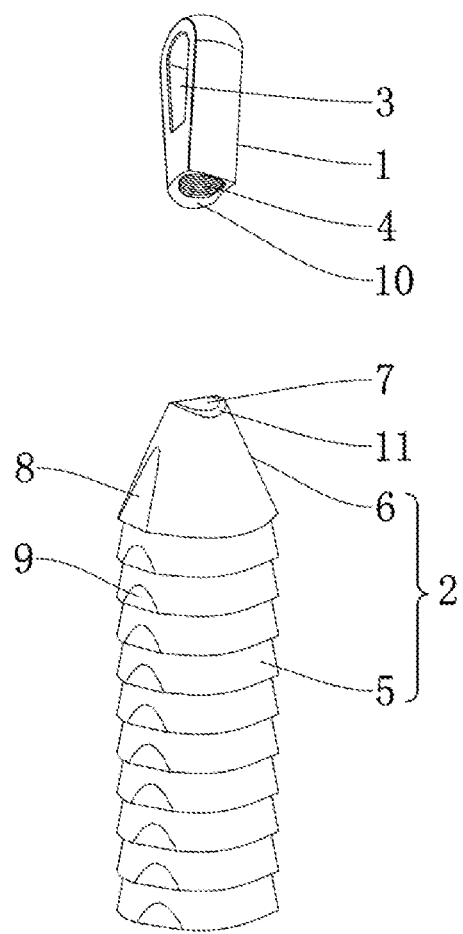
FIG. 3 is a schematic diagram of the structure according to a second embodiment.

As shown in FIG. 3, a suture anchor includes an anchor head 1 and an anchor body 2, the top of the anchor head 1 is a convex arc shape, and a threading hole 3 is formed on the front face of the anchor head 1. A first arc surface 10, which is concave from both sides to the middle, is formed on the bottom of the anchor head 1, and a screw hole 4 is formed in the center of the first arc surface 10.

As shown in FIG. 3, the anchor body 2 includes a side pressing portion 5 integrally formed by ten layers of round tables, and an abutment portion 6 integrally formed on the top of the side pressing portion 5. A through hole 7 for passing through an anchor operating handle is formed in the middle of the anchor body 2. The abutment portion 6 has a round table shape, and the taper of the abutment portion 6 is greater than that of the side pressing portion 5. A second arc surface 11, which protrudes from both sides to the middle, is formed on the top of the abutment portion 6, and the second arc surface 11 can abut on and fit with the first arc surface 10.

As shown in FIG. 3, oblique cuts 8 are formed on the front and back sides of the abutment portion 6. The oblique cut 8 has a shallow cutting depth at a position close to the top end of the abutment portion 6, and has a deep cutting depth at a position close to the lower end of the abutment portion 6. Longitudinal cuts 9 are formed on both the front and back sides of each round table of the side pressing portion 5, and each longitudinal cut 9 cuts the round table of the abutment portion 6 in the vertical direction. The positions of the longitudinal cuts 9 on the adjacent round tables from top to bottom have a small angular deflection toward the same direction.

Specific use process is as follows.

In use, the anchor head 1 and the anchor body 2 are connected to the anchor operating handle, the suture thread is passed through the threading hole 3, and the anchor head 1 and the anchor body 2 are pushed into a groove opened on the bone with the anchor operating handle.

The outer ring of the abutment portion 6 abuts on and fits to the inner wall of a groove opened on the bone for fixation. When the first arc surface 10 abuts on the second arc surface 11, a right edge of a longitudinal cut 9 on the round table closest to the anchor head 1 directly faces the threading hole 3, and a left edge of a longitudinal cut 9 on the round table furthest from the anchor head 1 directly faces the threading hole 3. Therefore, when the suture thread is stretched and straightened outwards, the suture thread can pass through a part with a larger gap between the abutment portion 6 and the bone groove, and can also pass through a part with a smaller gap therebetween, so that the suture thread is firmly fixed and cannot be cut off by the edge of the round table.

Embodiment 3

Figure 4:
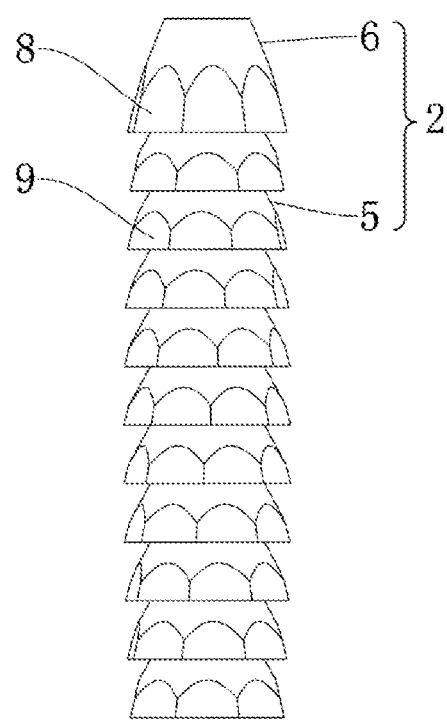
FIG. 4 is a schematic diagram of the structure of an anchor body according to a third embodiment.

This embodiment differs from the embodiment 1 is only in the anchor body 2. As shown in FIG. 4, the anchor body 2 includes a side pressing portion 5 integrally formed by a plurality of layers of round tables, and an abutment portion 6 integrally formed on the top of the side pressing portion 5. The abutment portion 6 has a round table shape, and the taper of the abutment portion 6 is greater than or equal to the taper of the round table of the side pressing portion 5. At least two oblique cuts 8 are uniformly formed on a circumference of the abutment portion 6 in the circumferential direction. Each oblique cut 8 has a shallow cutting depth at a position close to the top end of the abutment portion 6, and has a deep cutting depth at a position close to the lower end of the abutment portion 6. Longitudinal cuts 9, which are equal in number to the oblique cuts 8, are uniformly formed on a circumference of each round table of the side pressing portion 5 in the circumferential direction. Each longitudinal cut 9 cuts the round table of the abutment portion 6 in the vertical direction. From the top view, the positions of the longitudinal cuts 9 on the adjacent round tables from top to bottom is deflected by an angle of 5 degrees in the clockwise direction. From the top view, the oblique cuts 8 have an angle of 5 degrees in the counterclockwise direction relative to the longitudinal cuts 9 on the adjacent side pressing portion 5.

Embodiment 4

Figure 5:
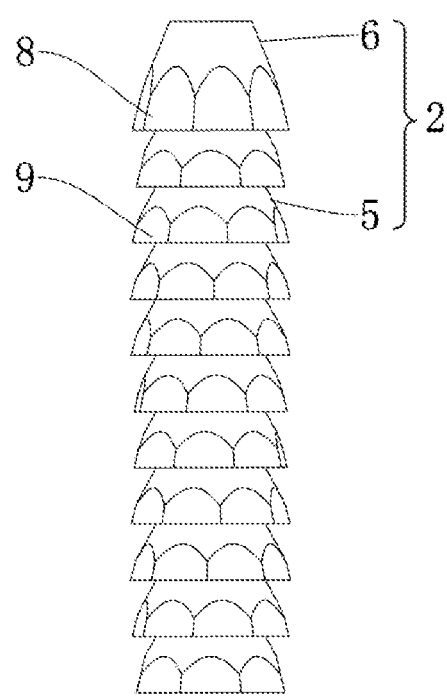
FIG. 5 is a schematic diagram of the structure of an anchor body according to a fourth embodiment.

This embodiment differs from the embodiment 1 is only in the anchor body 2. As shown in FIG. 5, the anchor body 2 includes a side pressing portion 5 integrally formed by a plurality of layers of round tables, and an abutment portion 6 integrally formed on the top of the side pressing portion 5. The abutment portion 6 has a round table shape, and the taper of the abutment portion 6 is greater than or equal to the taper of the round table of the side pressing portion 5. At least two oblique cuts 8 are uniformly formed on a circumference of the abutment portion 6 in the circumferential direction. Each oblique cut 8 has a shallow cutting depth at a position close to the top end of the abutment portion 6, and has a deep cutting depth at a position close to the lower end of the abutment portion 6. Longitudinal cuts 9, which are equal in number to the oblique cuts 8, are uniformly formed on a circumference of each round table of the side pressing portion 5 in the circumferential direction. Each longitudinal cut 9 cuts the round table of the abutment portion 6 in the vertical direction. From the top view, the positions of the longitudinal cuts 9 on the adjacent round tables from top to bottom is deflected by an angle of 10 degrees in the clockwise direction. From the top view, the oblique cuts 8 have an angle of 10 degrees in the counterclockwise direction relative to the longitudinal cuts 9 on the adjacent side pressing portion 5.

Embodiment 5

Figure 6:
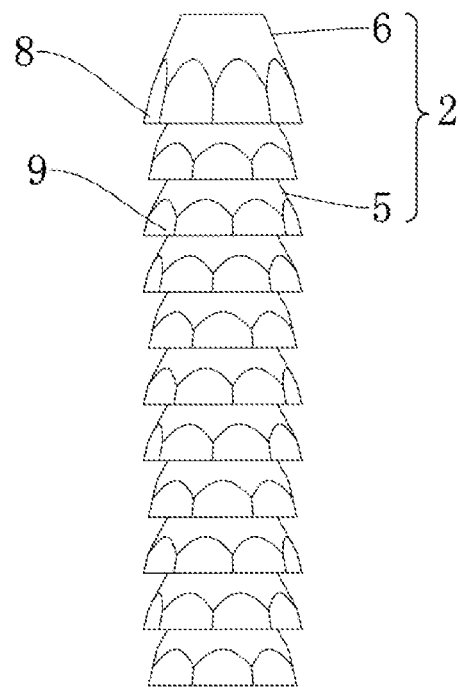
FIG. 6 is a schematic diagram of the structure of an anchor body according to a fifth embodiment.

This embodiment differs from the embodiment 1 is only in the anchor body 2. As shown in FIG. 6, the anchor body 2 includes a side pressing portion 5 integrally formed by a plurality of layers of round tables, and an abutment portion 6 integrally formed on the top of the side pressing portion 5. The abutment portion 6 has a round table shape, and the taper of the abutment portion 6 is greater than or equal to the taper of the round table of the side pressing portion 5. At least two oblique cuts 8 are uniformly formed on a circumference of the abutment portion 6 in the circumferential direction. Each oblique cut 8 has a shallow cutting depth at a position close to the top end of the abutment portion 6, and has a deep cutting depth at a position close to the lower end of the abutment portion 6. Longitudinal cuts 9, which are equal in number to the oblique cuts 8, are uniformly formed on a circumference of each round table of the side pressing portion 5 in the circumferential direction. Each longitudinal cut 9 cuts the round table of the abutment portion 6 in the vertical direction. From the top view, the positions of the longitudinal cuts 9 on the adjacent round tables from top to bottom is deflected by an angle of 15 degrees in the clockwise direction. From the top view, the oblique cuts 8 have an angle of 15 degrees in the counterclockwise direction relative to the longitudinal cuts 9 on the adjacent side pressing portion 5.

Embodiment 6

Figure 7:
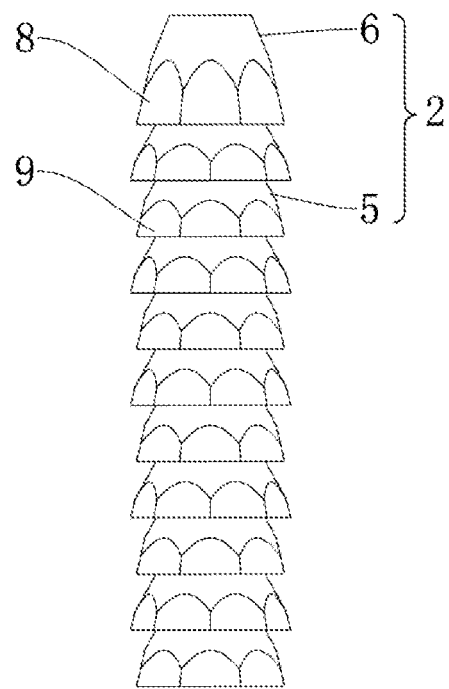
FIG. 7 is a schematic diagram of the structure of an anchor body according to a sixth embodiment.

This embodiment differs from the embodiment 1 is only in the anchor body 2. As shown in FIG. 7, the anchor body 2 includes a side pressing portion 5 integrally formed by a plurality of layers of round tables, and an abutment portion 6 integrally formed on the top of the side pressing portion 5. The abutment portion 6 has a round table shape, and the taper of the abutment portion 6 is greater than or equal to the taper of the round table of the side pressing portion 5. At least two oblique cuts 8 are uniformly formed on a circumference of the abutment portion 6 in the circumferential direction. Each oblique cut 8 has a shallow cutting depth at a position close to the top end of the abutment portion 6, and has a deep cutting depth at a position close to the lower end of the abutment portion 6. Longitudinal cuts 9, which are equal in number to the oblique cuts 8, are uniformly formed on a circumference of each round table of the side pressing portion 5 in the circumferential direction. Each longitudinal cut 9 cuts the round table of the abutment portion 6 in the vertical direction. From the top view, the positions of the longitudinal cuts 9 on the adjacent round tables from top to bottom is deflected by an angle of 45 degrees in the counterclockwise direction. From the top view, the oblique cuts 8 have an angle of 45 degrees in the clockwise direction relative to the longitudinal cuts 9 on the adjacent side pressing portion 5.

The above are the preferred embodiments of the present application, and the protection scope of the present application is not limited accordingly. Therefore, all equivalent changes made according to the structure, shape and principle of the present application should be covered within the scope of protection of the present application.

List of reference signs: 1. anchor head; 2. anchor body; 3. threading hole; 4. screw hole; 5. side pressing portion; 6. abutment portion; 7. through hole; 8. oblique cuts; 9. longitudinal cut; 10. first arc surface; 11. second arc surface.

What is claimed is:

1. A suture anchor, comprising an anchor head and an anchor body, wherein, a threading hole is formed on the anchor head, the anchor body comprises a side pressing portion integrally formed by a plurality of layers of round tables, and at least two opposite longitudinal cuts are formed on each round table of the side pressing portion; from a direction close to the anchor head to a direction away from the anchor head, positions of the longitudinal cuts on adjacent round tables are deflected toward a same side;

wherein, the anchor body further comprises an abutment portion located at an end of the side pressing portion close to the anchor head, the abutment portion has a round table shape, and a taper of the abutment portion is greater than the plurality of layers of round tables of the side pressing portion;

wherein, a first arc surface that is concave from both sides to the middle is formed on bottom of the anchor head, and a second arc surface that protrudes from both sides to the middle is formed on top of the abutment portion, and the second arc surface and the first arc surface fit with each other when being abutted tightly.

2. The suture anchor according to claim 1, wherein, the positions of the longitudinal cuts on adjacent round tables are deflected by a same angle in a clockwise or counterclockwise direction from a top view, and a deflection angle of the longitudinal cuts on the adjacent round tables is from 0 to 45 degrees.

3. The suture anchor according to claim 1, wherein, at least four longitudinal cuts are formed uniformly on each round table of the side pressing portion along a circumferential circle.

4. The suture anchor according to claim 1, wherein, the number of longitudinal cuts on each layer round table of the side pressing portion is two; when the first arc surface abuts on the second arc surface, a side edge of a longitudinal cut on the round table nearest to the anchor head directly faces the threading hole, and the other side edge of the longitudinal cut on the round table furthest from the anchor head directly faces the threading hole.

5. The suture anchor according to claim 1, wherein, a plurality of oblique cuts are uniformly formed on a circumference of the abutment portion in a circumferential direction, and a cutting depth of the oblique cut at a position near a lower end of the abutment portion is greater than a cutting depth at a position near a top end of the abutment portion.

6. The suture anchor according to claim 1, wherein, the top of the anchor head is a convex arc shape.

7. The suture anchor according to claim 1, wherein, a screw hole is formed on the bottom of the anchor head.

* * * * *